United States Patent [19]
Fukushima et al.

[11] Patent Number: 6,165,724
[45] Date of Patent: Dec. 26, 2000

[54] **OLIGONUCLEOTIDES FOR DETECTING ENTERIC HEMORRHAGIC *E.COLI* AND DETECTION METHOD USING THE SAME**

[75] Inventors: Shigeru Fukushima, Otsu; Naoko Takaoka, Kameoka, both of Japan

[73] Assignee: Shimadzu Corporation, Kyoto, Japan

[21] Appl. No.: 09/313,968

[22] Filed: May 19, 1999

[30] Foreign Application Priority Data

May 29, 1998 [JP] Japan ................... 10-149749

[51] Int. Cl.⁷ .............. C12Q 1/68; C12P 19/34; C07H 21/02; C07H 21/04
[52] U.S. Cl. ............ 435/6; 435/91.2; 536/23.1; 536/24.3; 536/24.32; 536/24.33; 536/26.6
[58] Field of Search ......... 435/6, 91.2; 536/23.1, 536/24.3, 24.32, 24.33, 26.6

[56] References Cited

U.S. PATENT DOCUMENTS 5,795,717  8/1998  Nakayama et al. .................. 435/6

OTHER PUBLICATIONS

Franke et al.,"Clonal Relatedness of Shiga–like Toxin–producing *Escherechia coli* o101 strains of Human and Porcine Origin", Journal of Clinical Microbiology, vol. 33 (12), pp. 3174–3178, Sep. 1995.

*Primary Examiner*—Jeffrey Fredman
*Assistant Examiner*—Arun Kv. Chakrabarti
*Attorney, Agent, or Firm*—Arent Fox Kintner Plotkin & Kahn, PLLC

[57] ABSTRACT

The object of the present invention is to provide a simple, rapid and highly sensitive method of examining EHEC or VTEC in the examination of food poisoning and diarrhea. In the present invention, the oligonucleotides of SEQ ID NOS: 1–9 hybridizing selectively with a Vero toxin gene from EHEC (or VTEC) or with an O antigen-synthesizing region gene from pathogenic *E. coli* O157 are prepared and used as primers for gene amplification. By this method, bacteria producing O157 as one of the pathogenic factors in these bacteria and *E. coli* capable of producing Vero toxin can be selectively detected.

5 Claims, 2 Drawing Sheets

<Used primers and amplification sizes>
- For VT1      : 349bp
- For VT2      : 112bp
- For O-157

<Gene carried by each strain>

| lane | sample | VT1 | VT2 | O-157 |
|------|--------|-----|-----|-------|
| ① | E.coli A | + | – | + |
| ② | E.coli B | – | + | + |
| ③ | E.coli C | + | + | + |
| ④ | E.coli D | + | + | + |
| ⑤ | E.coli E | + | + | + |
| ⑥ | E.coli F | + | + | – |
| ⑦ | E.coli G | + | – | – |
| ⑧ | E.coli H | – | + | – |
| ⑨ | E.coli I | – | – | – |
| ⑩ | Q water | – | – | – |

M: DNA size marker (Hinc II digest of φ174)

⟨Used primers and amplification sizes⟩

- For VT1 : 349bp
- For VT2 : 112bp
+
For O-157

⟨Gene carried by each strain⟩

| lane | sample | VT1 | VT2 | O-157 |
|---|---|---|---|---|
| ① | E.coli A | + | − | + |
| ② | E.coli B | − | + | + |
| ③ | E.coli C | + | + | + |
| ④ | E.coli D | + | + | + |
| ⑤ | E.coli E | + | + | + |
| ⑥ | E.coli F | + | + | − |
| ⑦ | E.coli G | + | − | − |
| ⑧ | E.coli H | − | + | − |
| ⑨ | E.coli I | − | − | − |
| ⑩ | Q water | − | − | − |

M: DNA size marker (Hinc II digest of φ174)

(C)

(A)

(B)

⟨Used primers and amplification sizes⟩

· For VT1      : 609bp
· For VT2      : 112bp
              +
      For O-157

⟨Gene carried by each strain⟩

| lane | sample | VT1 | VT2 | O-157 |
|---|---|---|---|---|
| ① | E. coli A | + | − | + |
| ② | E. coli B | − | + | + |
| ③ | E. coli C | + | + | + |
| ④ | E. coli D | + | + | + |
| ⑤ | E. coli E | + | + | + |
| ⑥ | E. coli F | + | + | − |
| ⑦ | E. coli G | + | − | − |
| ⑧ | E. coli H | − | + | − |
| ⑨ | E. coli I | − | − | − |
| ⑩ | Q water | − | − | − |

M: DNA size marker (Hinc II digest of φ174)

(C)

(A)

(B)

OLIGONUCLEOTIDES FOR DETECTING ENTERIC HEMORRHAGIC E.COLI AND DETECTION METHOD USING THE SAME

BACKGROUND OF THE INVENTION

1. Field of the Invention

The present invention relates to clinical examination and the examination of food qualities, particularly the examination of food poisoning or the detection and identification of EHEC or VTEC in the examination of diarrhea.

2. Disclosure of the Related Art

EHEC (or VTEC) as a causative bacterium for enteric hemorrhagic E. coli symptoms is found to be a microorganism causing not only food poisoning represented by hemorrhagic E. coli symptoms but also the hemolytic uremic syndrome as a severe disorder in infants, and in recent years, the detection of this microorganism came to be regarded as important in clinical examination.

Major materials to be examined in the examination of EHEC (or VTEC) are patient' stools, foods, or water (drinking water, river water etc.) collected around the patient. To detect and identify EHEC or VTEC from these samples, the procedures of direct separation and culture, a culture test for primary confirmation, a culture test for secondary confirmation, an agglutination test by anti-serum and a toxin production test should be conducted. However, the time required for each of these steps for culture ranges 18 to 24 hours, and the required total time is 3 to 4 days, so the examination is very time-consuming. Accordingly, the present-day method of examining EHEC (or VTEC) lacks in rapidness and simplicity, thus failing to serve as a practical means. Meanwhile, it was revealed that the serotype of EHEC (or VTEC) is typically O157:H7, which accounts for 80% or more of enteric hemorrhagic E. coli symptoms.

SUMMARY OF THE INVENTION

The object of the present invention is to provide a method of detecting a Vero (phonetic transcription) toxin gene and an O157 antigen-synthesizing region gene as pathogenic factors in EHEC (or VTEC) by gene amplification techniques using oligonucleotides functioning as primers in the reaction of synthesizing nucleic acids. The object of the present invention is to provide a simple, rapid and highly sensitive clinical examination particularly in the examination of food poisoning and diarrhea, particularly enteric hemorrhagic E. coli symptoms causing severe disorders.

The present invention relates to oligonucleotides for selectively detecting Vero toxin-producing E. coli (referred to hereinafter as VTEC) in EHEC (or VTEC) and pathogenic E. coli O157 accounting for the majority thereof, or to a mixture solution of oligonucleotides chemically synthesized so as to be complementary to target oligonucleotides each coding for Vero toxin 1 type (VT1) gene, Vero toxin 2 type (VT2) gene, Vero toxin 2 type mutants (VT2vha, VT2vhb, VT2vp1, and VT2vp2), and an O antigen-synthesizing region gene from pathogenic E. coli O157.

That is, according to the present invention, oligonucleotides hybridizing selectively with the Vero toxin genes from EHEC (or VTEC) or with the O157 antigen synthesizing region gene from E. coli are prepared and used as primers in gene amplification. By this method, those microorganisms having the Vero toxin gene or those microorganisms having the O157 serotype can be selectively detected in pathogenic E. coli.

Here, these primers have one of SEQ ID NOS: 1–9, as follows.

SEQ ID NO: 1:
   (5')d-CAACACTGGATGATCTCAG-(3') . . . (a)
SEQ ID NO: 2:
   (5')d-ATCAGTCGTCACTCACTGGT-(3') . . . (b)
SEQ ID NO: 3:
   (5')d-CCCCCTCAACTGCTAATA-(3') . . . (c)
SEQ ID NO: 4:
   (5')d-CTGCTGTCACAGTGACAAA-(3') . . . (d)
SEQ ID NO: 5:
   (5')d-ATCATTGACGATTGTAGCACC-(3') . . . (e)
SEQ ID NO: 6:
   (5')d-GTATTTGGAGACATCGGAGC-(3') . . . (f)
SEQ ID NO: 7:
   (5')d-ACATGAGGAGCATTAACTTCG-(3') . . . (g)
SEQ ID NO: 8:
   (5')d-ACTAATGACACGATTCGTTCC-(3') . . . (h)
SEQ ID NO: 9:
   (5')d-CTGAATCCCCCTCCATTATG-(3') . . . (i)

Further, these primers are used preferably in any of the following combinations:

Combination (1):
   (5')d-CAACACTGGATGATCTCAG-(3') . . . (a)
   (5')d-ATCACTCGTCACTCACTGGT-(3') . . . (b)
   (5')d-CCCCCTCAACTGCTAATA-(3') . . . (c)
   (5')d-CTGCTGTCACAGTGACAAA-(3') . . . (d)
   (5')d-ATCATTGACGATTGTAGCACC-(3') . . . (e)
   (5')d-ACATGAGGAGCATTAACTTCG-(3') . . . (g)

Combination (2):
   (5')d-CAACACTGGATGATCTCAG-(3') . . . (a)
   (5')d-ATCAGTCGTCACTCACTGGT-(3') . . . (b)
   (5')d-CCCCCTCAACTGCTAATA-(3') . . . (c)
   (5')d-CTGCTGTCACAGTGACAAA-(3') . . . (d)
   (5')d-GTATTTGGAGACATGGGAGC-(3') . . . (f)
   (5')d-ACTAATGACACGATTCGTTCC-(3') . . . (h)

Combination (3):
   (5')d-CAACACTGGATGATCTCAG-(3') . . . (a)
   (5')d-ATCAGTCGTCACTCACTGGT-(3') . . . (b)
   (5')d-CTGCTGTCACAGTGACAAA-(3') . . . (d)
   (5')d-ATCATTGACGATTGTAGCACC-(3') . . . (e)
   (5')d-ACATGAGGAGCATTAACTTCG-(3') . . . (g)
   (5')d-CTGAATCCCCCTCCATTATG-(3') . . . (i)

Combination (4):
   (5')d-CAACACTGGATGATCTCAG-(3') . . . (a)
   (5')d-ATCAGTCGTCACTCACTGGT-(3') . . . (b)
   (5')d-CTGCTGTCACAGTGACAAA-(3') . . . (d)
   (5')d-GTATTTGGAGACATGOGAGC-(3') . . . (f)
   (5')d-ACTAATGACACGATTCGTTCC-(3') . . . (h)
   (5')d-CTGAATCCCCCTCCATTATG-(3') . . . (i)

In detection of E. coli having O157 antigen and E. coli capable of producing Vero toxin, high detection sensitivity due to gene amplification and high selectivity due to the reaction defined by 2 or more primers can be achieved according the present invention by using the PCR techniques and by combining primers targeting the O antigen-synthesizing region gene in pathogenic E. coli as primary causative bacteria for enteric hemorrhagic E. coli symptoms, with primers targeting the Vero toxin gene as one of the pathogenic factors in enteric hemorrhagic E. coli. Further, because of highly sensitive detection, a large amount of a sample is not required, and the pretreatment of the sample can be simple. In the Example in the present invention, the reaction time was 3 hours and the operation time was 30 minutes. In addition, by use of agarose gel electrophoresis and a method of staining nucleic acids with ethidium bromide for detection, the detection can be effected without labeling the primers etc. Furthermore, because the lengths of the amplified nucleotides can be confirmed, the test result is highly reliable.

The examination of enteric hemorrhagic *E. coli* symptoms requires accurate results without delay for the necessity of rapid and suitable therapy and preventive treatment for the found patient.

Further, the present invention is to selectively detect the gene for the sugar-chain antigen constituting a part of the body of pathogenic *E. coli* O157 as major causative bacteria for enteric hemorrhagic *E. coli* symptoms, as well as the Vero toxin gene that is the pathogenic factor in said bacteria. Therefore, the detection and determination of the causative bacteria for enteric hemorrhagic *E. coli* symptoms can be effected rapidly and accurately according to the present invention.

DETAILED DESCRIPTION OF THE INVENTION

Figure 1:
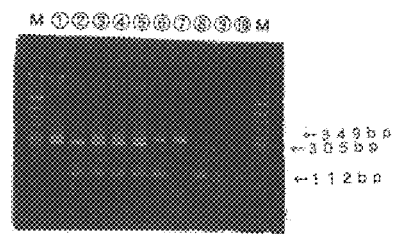
In FIG. 1, (A) shows a profile in electrophoresis where primer combination (1) was used; (B) shows a profile in electrophoresis where primer combination (2) was used; and (C) shows genes possessed by each strain.
Figure 1:
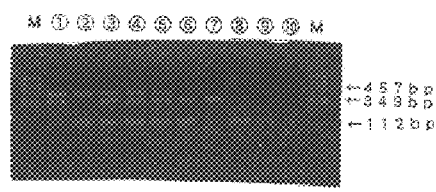

Gene amplification is conducted on the basis of polymerase chain reaction (abbreviated hereinafter to PCR; Science 230, 1350 (1985)) developed by Saiki et al. To detect specific nucleotide sequence regions (that is, in the present invention, the Vero toxin genes in EHEC or VTEC and the antigen-synthesizing region gene in *E. coli* O157) in this method, oligonucleotides which recognize and hybridize respectively with the + chain at one terminal and the − chain at the other terminal of each of said regions are prepared and used as primers, with which a nucleic acid sample previously rendered single-stranded by thermal denaturation is subjected to temperate-dependent nucleotide polymerization reaction, and the double-stranded nucleic acid thus formed is separated into single-stranded chains which are then subjected to the same reaction. By repeatedly conducting a series of these procedures, the copy number of the region sandwiched between the 2 primers is increased to permit its detection.

The sample may be any sample clinically examined, such as stool, urine, blood, tissue homogenate etc. or food materials. To use these materials as PCR samples, the operation of releasing nucleic acid components from bacteria present in the materials is required as pretreatment. However, because PCR will proceed in the presence of a few to dozens of nucleic acids with which the primers can hybridize, mere treatment of the test sample in a short time with a lytic enzyme, a surface active agent, an alkali etc. gives a sample solution containing nucleic acids in an amount enough to permit PCR to proceed. The oligonucleotides used as primers in the present invention may be chemically synthesized or naturally occurring nucleotide fragments each having a length of 10 bases or more, preferably 15 bases or more in view of selectivity, detection sensitivity, and reproducibility. The primers may particularly not have been labeled for detection.

The region to be amplified in the nucleotide region of the O antigen-synthesizing region gene from pathogenic *E. coli* O157 may be 50 to 2,000 bases, preferably 100 to 1,000 bases. For the template-dependent nucleotide polymerization reaction, thermostable DNA polymerase is used, but the source of this enzyme is not limited insofar as it maintains its activity at a temperature of 90 to 95° C. The temperature for the thermal denaturation is 90 to 95° C., the temperature for the annealing operation for hybridizing the primers is 37 to 65° C., and the temperature for the polymerization reaction is 50 to 75° C., and assuming these procedures are 1 cycle, 20 to 42 cycles of PCR are conducted for amplification.

For detection, the reaction solution after PCR is subjected directly to agarose gel electrophoresis whereby the presence and lengths of the amplified nucleotide fragments can be confirmed. From this result, it can be judged whether or not a nucleotide having the sequence to be recognized by the primers is present in the sample. This judgement is directly indicative of whether *E. coli* having the O157 antigen-synthesizing region gene is present or not. To detect the amplified nucleotide fragments, other electrophoresis or chromatography is also effective. Further, one of the above primers may be used as a probe to selectively detect the target nucleotide sequence on film or other carriers.

EXAMPLES

Example 1

Preparation of sample 347 strains in total of EHEC (or VTEC) derived from patients were used. Each strain was inoculated into an LB medium.(1% trypton, 0.5% yeast extract, and 1% sodium chloride) and cultured overnight at 37° C. under aerobic conditions with shaking. Each culture solution was diluted 10-fold with 10 mM Tris-HCl buffer, pH 7.5 (referred to hereinafter as TE buffer), subjected to thermal treatment at 95° C. for 10 minutes, and centrifuged, and the resulting supernatant was used as a sample.

Synthesis of primers

The respective sequences shown in SEQ ID NOS: 1–9 were those selected from the nucleotide sequences of the Vero toxin genes and the O antigen-synthesizing region gene, derived from EHEC strains having the serotype of O157 and producing Vero toxin. Then, oligonucleotides having the same sequences as in SEQ ID NOS: 1–9 were chemically synthesized. This chemical synthesis was performed by the β-cyanoethylphosphamidite method. The oligonucleotides thus synthesized were purified by high performance liquid chromatography on a C18 reverse phase column.

PCR 17.05 µl sterilized distilled buffer, 3 µl of 10× reaction buffer, 4.8 µl dNTP solution, 1.0 µl primer (1), 1.0 µl primer (2), and 0.15 µl thermostable DNA polymerase were added to 3 µl of the above sample solution to prepare 30µl reaction solution. 50µl mineral oil (SIGMA) was added to a vessel containing this reaction solution and layered on the reaction solution. The respective solutions used are as follows:

10× Reaction buffer: 500 mM KCl, 100 mM Tris-HCl, pH 8.3, 15 mM magnesium chloride, 0.1% (w/v) gelatin dNTP solution: a solution containing dATP, dCTP, dGTP and dTTP respectively at the final concentration of 1.25 mM Primers (1) and (2): an aqueous solution of the above-described chemically synthesized purified materials (concentration: 3.75 OD/ml)

Primer combination: The above chemically synthesized purified materials were used. Their combination is as defined in claim 3.

Thermostable DNA polymerase: Taq DNA polymerase (5 units/ml, a product of Perkin Elmer Cetus).

The reaction conditions are as follows:

Thermal denaturation: 94° C., 1 minute;

Annealing: 55° C., 1 minute; and

Polymerization reaction: 72° C., 1 minute.

35 cycles of PCR, each cycle consisting of a process of from thermal treatment via annealing to polymerization reaction, were conducted (about 3 hours in total). These procedures were performed in a DNA Thermal Cycler (Perkin Elmer Cetus) with the above conditions previously programmed.

Detection

To detect the nucleotide fragments amplified in the reaction solution, agarose gel electrophoresis was conducted in the following manner.

Agarose gel had a gel concentration of 3% (w/v), and contained ethidium bromide (0.5 µgl/ml). Electrophoresis was conducted at a constant voltage of 100 V for 30 minutes. The procedure and other conditions were in accordance with those described in Maniatis et al. Molecular Cloning, 2nd Ed. (1989). Molecular markers were also electrophoresed along the reaction solution so that the lengths of the nucleotide fragments could be determined from their relative mobility.

Agglutination test by anti-O157 serum

Whether the O antigen of the strains used was O157 or not was examined by an agglutination test using a commercial anti-O157 serum (Denka Seiken). The agglutination test was carried out in accordance with the manufacturer's instructions.

Results

The nucleotide sequence of the O157 antigen-synthesizing region gene from *E. coli* has already been determined as described above, and the sizes of the oligonucleotides of the present invention, that is, the nucleotides to be amplified with the primers by PCR can be easily estimated as shown in Table 1.

TABLE 1

| Primer combination | Estimations (bases) of PCR amplification products | | |
|---|---|---|---|
| | O157 antigen-synthesizing region gene | VT1 gene | VT2 gene |
| (1) | 305 | 349 | 112 |
| (2) | 457 | 349 | 112 |
| (3) | 305 | 609 | 112 |
| (4) | 457 | 609 | 112 |

For example, in primer combination (1), the nucleotide of 305 bases (or 305 base pairs) in length must be amplified as an amplification product of the O157 antigen-synthesizing region gene.

Further, as amplification products of the respective Vero toxin 1 and 2 type genes, the nucleotides of 349 bases (or 349 base pairs) and 112 bases (or 112 base pairs) are to be amplified respectively.

If these estimated values agree with the lengths of the actually amplified nucleotides, it was judged that this primer combination amplifies the target gene regions correctly and simultaneously the corresponding strain possesses the target genes.

That is, in primer combination (1), if the 3 amplified nucleotides of 305, 349, and 112 bases (or base pairs) are detected, then the examined strain is judged to possess the O157 antigen-synthesizing region gene and the VT1 and VT2 genes, to have the serotype of O157, and to produce Vero toxin 1 and 2 types respectively. If the nucleotide of 305 bases (or base pairs) is not detected and simultaneously only the amplified nucleotide of the VT2 type gene is detected, then the strain is judged to be Vero toxin-producing *E. coli* having a serotype other than O157.

Figure 2:
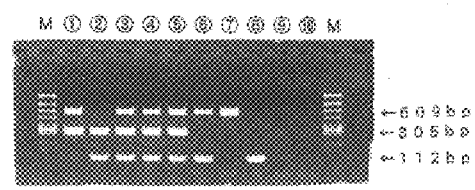
In FIG. 2, (A) shows a profile in electrophoresis where primer combination (3) was used; (B) shows a profile in electrophoresis where primer combination (4) was used; and (C) shows genes possessed by each strain.
Figure 2:
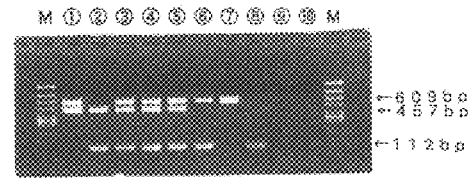

The detection results are shown in FIGS. 1 and 2. FIG. 1 (A) shows a profile in electrophoresis where primer combination (1) was used, FIG. 1 (B) shows a profile in electrophoresis where primer combination (2) was used; FIG. 2 (A) shows a profile in electrophoresis where primer combination (3) was used; and FIG. 2 (B) shows a profile in electrophoresis where primer combination (4) was used. (C) in FIGS. 1 and 2 shows lanes in the profile in electrophoresis.

As shown in FIGS. 1 and 2, each primer combination amplified its target gene regions exclusively and did not react with other gene regions at all. That is, it correctly amplifies the O157 antigen-synthesizing region gene and the VT1 and VT2 genes from *E. coli*, thereby enabling accurate detection of enteric hemorrhagic *E. coli*.

What is claimed is:

1. An oligonucleotide for selectively detecting Vero toxin producing *E. coli*, wherein said oligonucleotide is selected from the group consisting of SEQ ID NOS:5, 6, 7, 8, and 9.

2. A mixture of oligonucleotides, wherein said oligonucleotides are chemically synthesized to be complementary to target oligonucleotides coding for Vero toxin 1 type gene, Vero toxin 2 type gene, Vero toxin 2 type mutants or an O antigen-synthesizing region gene from pathogenic *E. coli* O157, and wherein said mixture comprises at least one oligonucleotide selected from the group consisting of SEQ ID NOS:5, 6, 7, 8, and 9.

3. The mixture of oligonucleotides according to claim 2, further comprising at least one oligonucleotide selected from the group consisting of SEQ ID NOS:1, 2, 3, and 4.

4. A mixture of oligonucleotides for detecting enteric hemorrhagic *E. coli* or Vero toxin producing *E. coli*, comprising oligonucleotides selected from the group consisting of:

SEQ ID NOS: 1, 2,3,4,5 and 7;
SEQ ID NOS: 1,2,3,4,6 and 8;
SEQ IDNOS: 1,2,4,5,7 and 9; and
SEQ ID NOS: 1, 2,4,6,8 and 9.

5. A method for detecting enteric hemorrhagic *E. coli* or Vero toxin producing *E. coli*, wherein at least one oligonucleotide according to claim 1 functions as a primer for a chain extension reaction to selectively amplify a target nucleotide sequence, comprising, a) hybridizing a primer with a single stranded target nucleic acid sequence and performing a chain extension reaction by polymerization of four kinds of nucleotides to produce a double stranded chain comprising the target nucleotide sequence;

b) separating the resulting double stranded chain into single stranded chains, wherein the complementary chain then functions as a template for a chain extension reaction by a second primer;

c) repeating steps a) and b) thereby amplifying the target nucleotide sequence;

d) detecting any amplified target nucleotide sequence by electrophoresis or chromatography as an indication of enteric hemorrhagic *E. coli* or Vero toxin producing *E. coli*.

* * * * *

SEQUENCE LISTING

<160> NUMBER OF SEQ ID NOS: 9

<210> SEQ ID NO 1
<211> LENGTH: 19
<212> TYPE: DNA
<213> ORGANISM: Escherichia coli

<400> SEQUENCE: 1
caacactgga tgatctcag                                              19

<210> SEQ ID NO 2
<211> LENGTH: 20

-continued

```
<212> TYPE: DNA
<213> ORGANISM: Escherichia coli

<400> SEQUENCE: 2
atcagtcgtc actcactggt                                               20

<210> SEQ ID NO 3
<211> LENGTH: 18
<212> TYPE: DNA
<213> ORGANISM: Escherichia coli

<400> SEQUENCE: 3
ccccctcaac tgctaata                                                 18

<210> SEQ ID NO 4
<211> LENGTH: 19
<212> TYPE: DNA
<213> ORGANISM: Escherichia coli

<400> SEQUENCE: 4
ctgctgtcac agtgacaaa                                                19

<210> SEQ ID NO 5
<211> LENGTH: 21
<212> TYPE: DNA
<213> ORGANISM: Escherichia coli

<400> SEQUENCE: 5
atcattgacg attgtagcac c                                             21

<210> SEQ ID NO 6
<211> LENGTH: 20
<212> TYPE: DNA
<213> ORGANISM: Escherichia coli

<400> SEQUENCE: 6
gtatttggag acatgggagc                                               20

<210> SEQ ID NO 7
<211> LENGTH: 21
<212> TYPE: DNA
<213> ORGANISM: Escherichia coli

<400> SEQUENCE: 7
acatgaggag cattaacttc g                                             21

<210> SEQ ID NO 8
<211> LENGTH: 21
<212> TYPE: DNA
<213> ORGANISM: Escherichia coli

<400> SEQUENCE: 8
actaatgaca cgattcgttc c                                             21

<210> SEQ ID NO 9
<211> LENGTH: 20
<212> TYPE: DNA
<213> ORGANISM: Escherichia coli

<400> SEQUENCE: 9
ctgaatcccc ctccattatg                                               20
```